United States Patent

Clough et al.

Patent Number: 5,206,245
Date of Patent: Apr. 27, 1993

[54] FUNGICIDAL AROMATIC PYRIMIDINYL OXIME ETHERS

[75] Inventors: John M. Clough, Marlow; Christopher R. A. Godfrey, Bracknell; Ian T. Streeting, Wokingham; Rex Cheetham, Bracknell; Paul J. de Fraine, Wokingham, all of England

[73] Assignee: Imperial Chemical Industries PLC, London, England

[21] Appl. No.: 736,168

[22] Filed: Jul. 26, 1991

[30] Foreign Application Priority Data

Jul. 27, 1990 [GB] United Kingdom ............... 9016584

[51] Int. Cl.$^5$ ............... A61K 31/505; C07D 239/26
[52] U.S. Cl. ............... 514/269; 514/274; 544/309; 544/310; 544/311; 544/312; 544/313; 544/314
[58] Field of Search ............... 544/319, 334, 309, 310, 544/311, 312, 313, 314; 514/269, 274

[56] References Cited

U.S. PATENT DOCUMENTS 4,829,085 5/1989 Wenderoth ............... 514/522
4,999,042 3/1991 Anthony ............... 71/88

FOREIGN PATENT DOCUMENTS 242081 3/1987 European Pat. Off. .
382375 1/1990 European Pat. Off. .

Primary Examiner—Mukund J. Shah
Assistant Examiner—Y. N. Gupta
Attorney, Agent, or Firm—William E. Dickheiser

[57] ABSTRACT

Fungicidal compounds having the formula (I):

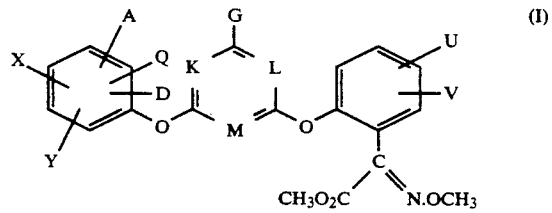

in which any two of K, L and M are nitrogen and the other is CE; X and Y are independently hydrogen, halogen, $C_{1-4}$ alkyl, $C_{3-6}$ cycloalkyl, $C_{2-4}$ alkenyl, $C_{2-4}$ alkynyl, $C_{2-4}$ alkynyloxy, phenyl, benzyloxy, cyano, isocyano, thiocyanato, isothiocyanato, nitro, $NR^1R^2$, $NR^1OR^2$, $N_3$, $NHCOR^1$, $NR^1CO_2R^2$, $NHCONR^1R^2$, $N=CHNR^1R^2$, $NHSO_2R^1$, $OR^1$, $OCOR^1$, $OSO_2R^1$, $SR^1$, $SOR^1$, $SO_2R^1$, $SO_2OR^1$, $SO_2NR^1R^2$, $COR^1$, $CR^1=NOR^2$, $CHR^1CO_2R^2$, $CO_2R^1$, $CONR^1R^2$, $CSNR^1R^2$, $CH_3O_2C.C:CH.OCH_3$, 1-(imidazol-1-yl)vinyl, a 5-membered heterocyclic ring containing one, two or three nitrogen heteroatoms, or a 5- or 6-membered heterocyclic ring containing one or two oxygen or sulphur heteroatoms, optionally a nitrogen heteroatom and optionally one or two oxo or thioxo substituents; or X and Y, when ortho to one another, join to form a 5- or 6-membered aliphatic or aromatic ring optionally containing one or two oxygen, sulphur or nitrogen atoms or one, two or three nitrogen atoms; A, Q, D, E, G, U and V are independently hydrogen, halogen (especially fluorine and chlorine), $C_{1-4}$ alkyl (especially methyl), $C_{1-4}$ alkoxy (especially methoxy), cyano, nitro or trifluoromethyl; and $R^1$ and $R^2$ are independently hydrogen, $C_{1-4}$ alkyl, $C_{2-4}$ alkenyl or phenyl; the aliphatic moieties of any of the foregoing being optionally substituted with one of more of halogen, cyano, $OR^1$, $SR^1$, $NR^1R^2$, $SiR^1_3$ or $OCOR^1$ and the phenyl moieties of any of the foregoing being optionally substituted with one or more of halogen, $C_{1-4}$ alkyl, $C_{1-4}$ alkoxy, nitro or cyano.

6 Claims, No Drawings

FUNGICIDAL AROMATIC PYRIMIDINYL OXIME ETHERS

This invention relates to derivatives of propenoic acid useful as fungicides, to processes for preparing them, to fungicidal compositions containing them, and to methods of using them to combat fungi, especially fungal infections of plants.

A range of pesticidal alkyl 2-(substituted)pyridinyl- and pyrimidinyloxyphenyl-3-alkoxypropenoates is described in EP-A-0242081.

According to the present invention there are provided pyrimidines having the formula (I), in which any two of K, L and M are nitrogen and the other is CE; X and Y are independently hydrogen, halogen, $C_{1-4}$ alkyl, $C_{3-6}$ cycloalkyl, $C_{2-4}$ alkenyl, $C_{2-4}$ alkenyl, $C_{2-4}$ alkynyloxy, phenyl, benzyloxy, cyano, isocyano, thiocyanato, isothiocyanato, nitro, $NR^1R^2$, $NR^1OR^2$, $N_3$, $NHCOR^1$, $NR^1CO_2R^2$, $NHCONR^1R^2$, $N=CHNR^1R^2$, $NHSO_2R^1$, $OR^1$, $OCOR^1$, $OSO_2R^1$, $SR^1$, $SOR^1$, $SO_2R^1$, $SO_2OR^1$, $SO_2NR^1R^2$, $COR^1$, $CR^1=NOR^2$, $CHR^1CO_2R^2$, $CO_2R^1$, $CONR^1R^2$, $CSNR^1R^2$, $CH_3O_2C.C=CH.OCH_3$, $CH_3O_2C.C=N.OCH_3$, 1-(imidazol-1-yl)vinyl, a 5-membered heterocyclic ring containing one, two or three nitrogen heteroatoms, of a 5- or 6-membered heterocyclic ring containing one or two oxygen or sulphur heteroatoms, optionally a nitrogen heteroatom and optionally one or two oxo or thioxo substituents; or X and Y, when ortho to one another, join to form a 5- or 6-membered aliphatic or aromatic ring optionally containing one or two oxygen, sulphur or nitrogen atoms or one, two or three nitrogen atoms; A, Q, D, E, G, U and V are independently hydrogen, halogen (especially fluorine and chlorine), $C_{1-4}$ alkyl (especially methyl), $C_{1-4}$ alkoxy (especially methoxy), cyano, nitro or trifluoromethyl; and $R^1$ and $R^2$ are independently hydrogen, $C_{1-4}$ alkyl, $C_{2-4}$ alkenyl or phenyl; the aliphatic moieties of any of the foregoing being optionally substituted with one or more of halogen, cyano, $OR^1$, $SR^1$, $NR^1R^2$, $SiR^1_3$ or $OCOR^1$ and the phenyl moieties of any of the foregoing being optionally substituted with one or more of halogen, $C_{1-4}$ alkyl, $C_{1-4}$ alkoxy, nitro or cyano.

Because of the unsymmetrically substituted double bond of the oxime ether group, the compounds of the invention may be obtained in the form of mixtures of (E) and (Z) geometric isomers (see under "Chemical Formulae" later). However, these mixtures can be separated into individual isomers, and this invention embraces such isomers and mixtures thereof in all proportions including those which consist substantially of the (Z)-isomer and those which consist substantially of the (E)-isomer. The (E)-isomer, in which the groups —$CO_2CH_3$ and —$OCH_3$ are on opposite sides of the carbon-nitrogen double bond of the oximes ether group, are the more fungicidally active and form a preferred embodiment of the invention.

Geometric pairs of isomers of the compounds listed later in Table I are identified by the letters A and B. In many instances, using solvent systems such as ether or ethyl acetate, or mixtures of one of these with petrol, the isomers A and B of a compound have significantly different $R_f$ values when analysed by thin-layer chromatography on silica gel. Of each pair of isomers the isomer which is the less polar on silica gel is termed Isomer A and the more polar one, Isomer B. In the case of the two geometric isomers of methyl O-methyl(2-phenoxyphenyl)oximinoacetate (compounds numbers 5 and 6 of Table I of EP-A-0254426), Isomer B has been shown unambiguously by X-ray analysis to be the (E)-isomer. It is believed that for every isomer pair, Isomer B corresponds to the (E)-isomer and Isomer A corresponds to the (Z)-isomer but this has not been proven. Generally the B isomers are the more active ones fungicidally and form a preferred embodiment of the invention.

Alkyl groups contain from 1 to 4 carbon atoms and may be in the form of straight or branched chains. Examples are methyl, ethyl, iso-propyl, n-butyl and t-butyl. Cycloalkyl groups contain from 3 to 6 carbon atoms and include cyclopropyl and cyclohexyl.

Alkenyl and alkynyl groups contain from 2 to 4 carbon atoms and may be in the form of straight or branched chains. Examples are ethenyl, allyl, methylallyl and propargyl.

Halogen is typically fluorine, chlorine or bromine.

Substituted aliphatic moieties include, in particular, halo($C_{1-4}$)alkyl, halo($C_{1-4}$)alkoxy, halo($C_{1-4}$)alkylthio, $CH_2OR^1$, $CH_2SR^1$ and $CH_2NR^1R^2$, wherein $R^1$ and $R^2$ are H, $C_{1-4}$ alkyl or phenyl.

Typical optional substituents of phenyl moieties are fluorine, chlorine, methyl, methoxy, nitro and cyano.

The ring containing the groups K, L and M in formula (I) is a pyrimidine ring which may be joined to the phenoxy groups by any two of its ring carbon atoms adjacent to a ring nitrogen atom. Of particular interest are those compounds of formula (I) in which K and L are both nitrogen and M is CH. Typically, one or both of X and Y are hydrogen. When one of X and Y is not hydrogen it is preferably attached to the 2-position of the phenyl ring.

Thus, in one aspect, the invention provides compounds of formula (I) in which K, L and M have the meanings previously given; X, which is preferably attached to the 2-position of the phenyl ring, is hydrogen, halogen (e.g. fluorine, chlorine or bromine), $C_{1-4}$ alkyl (e.g. methyl or ethyl), $C_{1-4}$ alkyl (especially methyl) substituted with halogen (e.g. fluorine, chlorine or bromine), hydroxy, cyano, $C_{1-4}$ alkoxy (e.g. methoxy) or $C_{1-4}$ alkanoyloxy (e.g. acetoxy), $C_{2-4}$ alkenyl (e.g. ethenyl, allyl or methylallyl), $C_{2-4}$ alkynyl (e.g. ethynyl or propargyl), $C_{2-4}$ alkenyloxy (e.g. allyloxy), $C_{2-4}$ alkynyloxy (e.g. propargyloxy), phenyl, benzyl, cyano, isocyano, thiocyanato, isothiocyanato, nitro, amino, mono- or di($C_{1-4}$)alkylamino (e.g. methylamino or dimethylamino), formylamino, $C_{1-4}$ alkanoylamino (e.g. acetamido), benzoylamino, ureido, phenylureido, $C_{1-4}$ alkylsulphonylamino (e.g. mesylamino), phenylsulphonylamino, hydroxy, $C_{1-4}$ alkoxy (e.g. methoxy or ethoxy), phenoxy, $C_{1-4}$ alkanoyloxy (e.g. acetoxy), $C_{1-4}$ alkylsulphonyloxy (e.g. mesyloxy), phenylsulphonyloxy, $C_{1-4}$ alkylthio (e.g. methylthio), $C_{1-4}$ alkylsulphinyl (e.g methylsulphinyl), $C_{1-4}$ alkylsulphonyl (e.g. mesyl or n-butylsulphonyl), formyl, $C_{1-4}$ alkanoyl (e.g. acetyl), benzoyl, hyroxyimino($C_{1-4}$)alkyl (e.g. hydroxyiminomethyl), $C_{1-4}$ alkoxyimino($C_{1-4}$)alkyl (e.g. methoxyiminomethyl), carbamoyl, $C_{1-4}$ alkylcarbamoyl (e.g. methylcarbamoyl), thiocarbamoyl or $C_{1-4}$ alkylthiocarbamoyl (e.g. methylthiocarbamoyl), the phenyl ring of any of the foregoing being optionally substituted with halogen (e.g. fluorine of chlorine), $C_{1-4}$ alkyl (e.g. methyl), $C_{1-4}$ alkoxy (e.g. methoxy), nitro or cyano; and Y is halogen (e.g. fluorine or chlorine), $C_{1-4}$ alkyl (e.g. methyl), $C_{1-4}$ alkoxy (e.g. methoxy), nitro, cyano or preferably, hydrogen, or X and Y, when ortho to one another, together form methylenedioxy, or together with the phenyl ring to which they are attached form a naphthalene, quinoline, benzimidazole or benzothienyl ring.

In another aspect the invention provides compounds of the formula (I.1), in which X is hydrogen, halogen (especially chlorine), $C_{1-4}$ alkyl (especially methyl), $C_{1-4}$ alkoxy (especially methoxy), trifluoromethyl, cyano, thiocarbamoyl or nitro, and Y is hydrogen or fluoro.

The invention is illustrated by the compounds listed in Tables I to III which follow. Compounds 1 to 160 in Table I have the formula (I.2), except for compound 9A which is the (Z)-isomer corresponding to compound 9B, in which X and Y have the values listed in the table. Compounds 161 to 199 in Table I have the formula (I.3) in which Ar has the values listed in the table. The compounds in Tables II and III have the formulae (I.4) and (I.5), respectively, in which Z is as defined in the tables.

TABLE I

| Compound No | X (see formula (I.2)) | Y |
|---|---|---|
| 1 | H | H |
| 2 | 2-F | H |
| 3 | 3-F | H |
| 4 | 4-F | H |
| 5 | 2-Cl | H |
| 6 | 3-Cl | H |
| 7 | 4-Cl | H |
| 8 | 2-Br | H |
| 9A | 2-Cyano | H |
| 9B | 2-Cyano | H |
| 10 | 3-Cyano | H |
| 11 | 4-Cyano | H |
| 12 | 2-Isocyano | H |
| 13 | 2-NO$_2$ | H |
| 14 | 3-NO$_2$ | H |
| 15 | 4-NO$_2$ | H |
| 16 | 2-NH$_2$ | H |
| 17 | 3-NH(CH$_3$) | H |
| 18 | 2-N(CH$_3$)$_2$ | H |
| 19 | 2-NH.CHO | H |
| 20 | 2-NH.COCH$_3$ | H |
| 21 | 3-NH.COC$_6$H$_5$ | H |
| 22 | 2-NH.CONH$_2$ | H |
| 23 | 3-NH.CONH(C$_2$H$_5$) | H |
| 24 | 2-NH.SO$_2$CH$_3$ | H |
| 25 | 3-NH.SO$_2$C$_6$H$_5$ | H |
| 26 | 2-OH | H |
| 27 | 3-OH | H |
| 28 | 4-OH | H |
| 29 | 2-OCH$_3$ | H |
| 30 | 3-OCH$_3$ | H |
| 31 | 4-OCH$_3$ | H |
| 32 | 2-OC$_2$H$_5$ | H |
| 33 | 3-(2-F—C$_6$H$_4$O) | H |
| 34 | 2-OCOCH$_3$ | H |
| 35 | 2-OSO$_2$CH$_3$ | H |
| 36 | 3-(4-CH$_3$—C$_6$H$_4$SO$_2$O) | H |
| 37 | 2-SCN | H |
| 38 | 3-SCN | H |
| 39 | 4-SCN | H |
| 40 | 2-SCH$_3$ | H |
| 41 | 3-SCH$_3$ | H |
| 42 | 4-SCH$_3$ | H |
| 43 | 2-S(O)CH$_3$ | H |
| 44 | 2-SO$_2$CH$_3$ | H |
| 45 | 4-SO$_2$(CH$_2$)$_3$CH$_3$ | H |
| 46 | 2-CHO | H |
| 47 | 3-CHO | H |
| 48 | 4-CHO | H |
| 49 | 2-COCH$_3$ | H |
| 50 | 3-COC$_6$H$_5$ | H |
| 51 | 2-(E)—CH=NOH | H |
| 52 | 3-(E)—CH=NOH | H |
| 53 | 4-(E)—CH=NOH | H |
| 54 | 2-(E)—CH=NOCH$_3$ | H |
| 55 | 2-(E)—C(CH$_3$)=NOH | H |
| 56 | 2-CONH$_2$ | H |
| 57 | 3-CONH(CH$_3$) | H |
| 58 | 4-CON(CH$_3$)$_2$ | H |
| 59 | 2-CSNH$_2$ | H |
| 60 | 2-CSNH(CH$_3$) | H |
| 61 | 2-CH$_3$ | H |
| 62 | 3-CH$_3$ | H |
| 63 | 4-CH$_3$ | H |
| 64 | 2-C$_2$H$_5$ | H |
| 65 | 2-CH$_2$F | H |
| 66 | 2-CH$_2$Br | H |
| 67 | 2-CH$_2$Cl | H |
| 68 | 2-CH$_2$CN | H |
| 69 | 2-CH$_2$OH | H |
| 70 | 2-CH$_2$OCH$_3$ | H |
| 71 | 2-CH$_2$OCOCH$_3$ | H |
| 72 | 3-CH$_2$CN | H |
| 73 | 4-CH$_2$OH | H |
| 74 | 3-CH$_2$OCH$_3$ | H |
| 75 | 2-CH=CH$_2$ | H |
| 76 | 2-CH$_2$CH=CH$_2$ | H |
| 77 | 2-C≡CH | H |
| 78 | 2-CH$_2$C≡CH | H |
| 79 | 3-CH$_2$C(CH$_3$)=CH$_2$ | H |
| 80 | 2-OCH$_2$CH=CH$_2$ | H |
| 81 | 2-OCH$_2$C≡CH | H |
| 82 | 2-C$_6$H$_5$ | H |
| 83 | 3-C$_6$H$_6$ | H |
| 84 | 4-C$_6$H$_5$ | H |
| 85 | 2-C$_6$H$_5$O | H |
| 86 | 3-C$_6$H$_5$O | H |
| 87 | 4-C$_6$H$_5$O | H |
| 88 | 2-(4-Cl—C$_6$H$_4$O) | H |
| 89 | 2-C$_6$H$_5$CH$_2$O | H |
| 90 | 2-Cyano | 4-Cl |
| 91 | 2-NO$_2$ | 4-F |
| 92 | 2-Cl | 4-Cl |
| 93 | 2-OCH$_3$ | 3-OCH$_3$ |
| 94 | 2-Cyano | 5-Cl |
| 95 | 2-Cyano | 6-Cyano |
| 96 | 2-F | 5-Cl |
| 97 | 3-OCH$_3$ | 5-OCH$_3$ |
| 98 | 3-Cyano | 4-F |
| 99 | 2-NO$_2$ | 3-OCH$_3$ |
| 100 | 3-OCH$_3$ | 5-Cyano |
| 101 | 2-CO$_2$CH$_3$ | H |
| 102 | 2-I | H |
| 103 | 2-CF$_3$ | H |
| 104 | 2-i-C$_3$H$_7$ | H |
| 105 | 2-i-C$_3$H$_7$O | H |
| 106 | 2-F | 6-F |
| 107 | 2-F | 4-F |
| 108 | 2-F | 3-F |
| 109 | 2-n-C$_3$H$_7$O | H |
| 110 | 2-n-C$_4$H$_9$O | H |
| 111 | 2-CH(OH)CH$_3$ | H |
| 112 | 2-t-C$_4$H$_9$ | H |
| 113 | 2-s-C$_4$H$_9$ | H |
| 114 | 2-n-C$_3$H$_7$ | H |
| 115 | 2-(E)—CH=CH(CH$_3$) | H |
| 116 | 2-Cyano | 4-OCH$_3$ |
| 117 | 2-Cyano | 5-OCH$_3$ |
| 118 | 2-Cyano | 4-Cl |
| 119 | 2-Cyano | 5-N(C$_2$H$_5$)$_2$ |
| 120 | 2-CONH$_2$ | H |
| 121 | 2-C≡CSi(CH$_3$)$_3$ | H |
| 122 | 2-F | 5-F |
| 123 | 2-(E)—CH$_3$O$_2$C.C=N.OCH$_3$ | H |
| 124 | 3-F | 5-F |
| 125 | 2-NHOH | H |
| 126 | 2-CH$_2$OCH$_3$ | H |
| 127 | 2-CH$_2$CN | H |
| 128 | 2-N$_3$ | H |
| 129 | 2-Cyano | 6-F |
| 130 | 2-NO$_2$ | 6-F |
| 131 | 2-CSNH$_2$ | 6-F |
| 132 | 2-Cyano | 3-F |
| 133 | 2-Cyano | 5-F |
| 134 | 2-Cyano | 3-OCH$_3$ |
| 135 | 2-Cyano | 6-OCH$_3$ |
| 136 | 2-NO$_2$ | 4-OCH$_3$ |
| 137 | 2-NO$_2$ | 5-OCH$_3$ |

TABLE I-continued

| | | |
|---|---|---|
| 138 | 2-NO$_2$ | 6-OCH$_3$ |
| 139 | 2-CSNH$_2$ | 3-OCH$_3$ |
| 140 | 2-CSNH$_2$ | 4-OCH$_3$ |
| 141 | 2-CSNH$_2$ | 5-OCH$_3$ |
| 142 | 2-CSNH$_2$ | 6-OCH$_3$ |
| 143 | 2-Cyano | 3-Cyano |
| 144 | 2-F | 3-Cyano |
| 144A | 2-OCH$_3$ | 3-Cyano |
| 145 | 3-Cyano | 6-F |
| 146 | * | H |
| 147 | * | H |
| 148 | * | H |
| 149 | * | H |
| 150 | 2-Cyano | 4-Br |
| 151 | 2-Cyano | 6-Br |
| 152 | 2-Cyano | 4-NO$_2$ |
| 153 | 2-Cyano | 6-NO$_2$ |
| 154 | 2-Cyano | 6-OC$_2$H$_5$ |
| 155 | 2-Cyano | 4-CO$_2$CH$_3$ |
| 156 | 2-Cyano | 6-CO$_2$C$_2$H$_5$ |
| 157 | 2-Cyano | 6-CH$_3$ |
| 158 | 2-Cyano | 5-CH$_2$C$_6$H$_5$ |
| 159 | 2-Cyano | 4-OCF$_3$ |
| 160 | 2-Cyano | 4-Cyano |

| Compound No | Ar (see formula (I.3)) |
|---|---|
| 161 | * |
| 162 | * |
| 163 | * |
| 164 | * |
| 165 | * |
| 166 | * |
| 167 | Pentafluorophenyl |
| 168 | 2,4,6-Tri-F—C$_6$H$_2$ |
| 169 | 2,3,5,6-Tetra-F—C$_6$H |
| 170 | 2,3,6-Tri-F—C$_6$H$_2$ |
| 171 | 2,3-Di-cyano-6-F—C$_6$H$_2$ |
| 172 | 2,6-Di-F-3-CH$_3$O—C$_6$H$_2$ |
| 173 | 2,6-Di-F-4-CH$_3$O—C$_6$H$_2$ |
| 174 | 2,6-Di-F-3-NO$_2$—C$_6$H$_2$ |
| 175 | 2,6-Di-F-4-NO$_2$—C$_6$H$_2$ |
| 177 | 4,6-Di-Br-2-cyano-C$_6$H$_2$ |
| 176 | 2,6-Di-F-3,5-di-CH$_3$O—C$_6$H |
| 178 | 3-Cyano-2,6-di-F—C$_6$H$_2$ |
| 179 | 6-Br-2-cyano-4-CH$_3$O—C$_6$H$_2$ |
| 180 | 6-Br-4-Cl-2-cyano-C$_6$H$_2$ |
| 181 | 6-Br-2-cyano-4-NO$_2$—C$_6$H$_2$ |
| 182 | 3-Br-2-cyano-6-CH$_3$O—C$_6$H$_2$ |
| 183 | 3,5-Di-Cl-2-cyano-C$_6$H$_2$ |
| 184 | 4,6-Di-Cl-2-cyano-C$_6$H$_2$ |
| 185 | 3-Br-2-cyano-4-CH$_3$O—C$_6$H$_2$ |
| 186 | 4-Br-2-cyano-6-NO$_2$—C$_6$H$_2$ |
| 187 | 4-Br-2-cyano-6-CH$_3$O—C$_6$H$_2$ |
| 188 | 2-Cyano-4-I-6-CH$_3$O—C$_6$H$_2$ |
| 189 | 2-Cyano-6-CH$_3$O-4-NO$_2$—C$_6$H$_2$ |
| 190 | 2-Cyano-4,6-di-NO$_2$—C$_6$H$_2$ |
| 191 | 2-Cyano-4-CH$_3$-6-NO$_2$—C$_6$H$_2$ |
| 192 | 2-Cyano-4-CH$_3$O-6-NO$_2$—C$_6$H$_2$ |
| 193 | 2-Cyano-5,6-di-CH$_3$O—C$_6$H$_2$ |
| 194 | 2-Cyano-5,6-di-CH$_3$O-3-CH$_3$—C$_6$H |
| 195 | 3,4-Di-Br-2-cyano-6-CH$_3$O—C$_6$H |
| 196 | 3-Br-2-cyano-6-CH$_3$O-4-NO$_2$—C$_6$H |
| 197 | 2-Cyano-6-CH$_3$CH$_2$O-4-NO$_2$—C$_6$H$_2$ |
| 198 | * |
| 199 | * |

*These values are given later under "Chemical Formulae".

TABLE II

Table II comprises 199 compounds of the general formula (I.4) wherein Z is X-Y-C$_6$H$_3$ or Ar which have all the values listed in Table I. That is, compounds numbers 1 to 199 of Table II are the same as those of Table I except that the pyrimidine ring is 4,6-disubstituted in Table I and 2,4-disubstituted as shown in Table II.

TABLE II

Table III comprises 199 compounds of the general formula (I.5) wherein Z is X-Y-C$_6$H$_3$ or Ar which have all the values listed in Table I. That is, compounds numbers 1 to 199 of Table III are the same as those of Table I except that the pyrimidine ring is 4,6-disubstituted in Table I and 2,4-disubstituted as shown in Table III.

The compounds of the invention of formula (I) [equivalent to (IA) when W is the group CH$_3$O$_2$C.C=N.OCH$_3$] can be prepared by the steps illustrated in Schemes I and II. Throughout these Schemes the terms X, Y, A, Q, D, G, U, V, K, L and M are as defined above; W is CH$_3$O$_2$O$_2$C.C=N.OCH$_3$ (or a group that can be transformed into CH$_3$O$_2$C.C=N.OCH$_3$ using methods previously described in EP-A-0254426); Z$^1$ and Z$^2$, which may be the same or different, are leaving groups (such as halogen or CH$_3$SO$_3$—), Z$^1$ being the leaving group which is more readily displaced if both Z$^1$ and Z$^2$ are present in the same compound or if Z$^1$ and Z$^2$ are both present in different compounds of a coupling reaction; T$^1$ is hydrogen or a metal (such as sodium); and T$^2$ is hydrogen, a metal (such as sodium) or a protecting group (such as benzyl). Each reaction shown in Schemes I and II is performed either in a suitable solvent or without a solvent, and at a suitable temperature.

Thus compounds of the invention of formula [(IA): W is the group CH$_3$O$_2$C.C=N.OCH$_3$] can be prepared by two successive reactions of the Ullmann type, using appropriately functionalised benzene and pyrimidine intermediates. The pathways shown in Schemes I and II illustrate that (i) the order of the steps by which these benzene and pyrimidine units are assembled can be varied; and (ii) the functional groups which react during the Ullmann coupling, namely an oxygen nucleophile and a leaving group on an aromatic ring, may be positioned on either of the substrates at each individual step.

For example, compounds of formula (IA) can be prepared from compounds of formula (II) by treatment with phenols of formula (III), wherein T$^1$ is hydrogen, in the presence of a base (such as potassium carbonate). Alternatively, compounds of formula (IA) can be prepared from compounds of formula (II) by treatment with phenolate salts of formula (III), wherein T$^1$ is a metal (such as sodium).

Compounds of formula (II) can be prepared by treatment of compounds of formula (IV) with phenols of formula (V), wherein T$^1$ is hydrogen, in the presence of a base (such as potassium carbonate). Alternatively, compounds of formula (II) can be prepared by treatment of compounds of formula (IV) with phenolate salts of formula (V), wherein T$^1$ is a metal (such as sodium).

Similarly, compounds of formula (II) can be prepared by allowing compounds of formula (VI) to react with compounds of formula (VII); when T$^1$ is hydrogen, the reaction is performed in the presence of a base (such as potassium carbonate).

The preparation of compounds of formula (IA) from intermediates (VIII), (XI) and (XII), as well as the preparation of these intermediates from the monocyclic precursors, is carried out by similar methods.

Modifications to the group W may be made at any appropriate stage in the pathways shown in Schemes I and II. For example, during one or more of the Ullman couplings, W may be the group COCO$_2$R or the group CH$_2$CO$_2$R (wherein R is H, CH$_3$ or a metal), to be converted at the last stages of the synthesis into the group CH$_3$O$_2$C.C=N.OCH$_3$ using, for example, one of the methods described in EP-A-0254426. When T$^2$ is a protecting group, it may be removed at any appropriate reaction step.

The substituents X, Y, A, B, D, E (one of K, L and M having the value CE, wherein E is as defined above), G, U and V may also be modified at any appropriate reaction step. For example, if X is $NO_2$ it may be converted via reduction an diazotisation into a halogen, CN or OH group, and this may be carried out on intermediates such as (XI) or (XII) or on the compunds of formula (IA). Or, for example, if G is a halogen such as chlorine, it may be removed at an appropriate stage of the synthesis (such as at the last stage) to give the corresponding pyrimidine in which G is hydrogen.

The intermediates of formulae (II) an d(VIII) may be interconverted using standard methods. The intermediates of formulae (XI) and (XII) are similarly interconvertible. Compounds of formulae (III), (IV), (VI), (IX), (X), (XIII), (XIV), (XV), (XVI) and (XVII) can be prepared by standard methods described in the chemical literature. Compounds of formulae (V) and (VII) can either be prepared by standard methods described in the chemical literature, or, when W id $CH_3O_2C.C≡N.OCH_3$, can be prepared by methods described in EP-A-0254426.

In a further aspect, the invention provides processes as herein described for preparing the compounds of the invention.

The compounds are active fungicides and may be used to control one or more of the following pathogens: *Pyricularia oryzae* on rice, *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such a *Sphaerotheca macularis* on hops, *Sphaerotheca fuliginea* on cucurbits (e.g. cucumber), *Podosphaera leucotricha* on apple and *Uncinula necator* on vines. Helminthosporium spp., Rhynchosporium spp., Septoria Spp., Pyrenophora spp., *Pseudocercosporella herpotrichoides* and *Gaeumannomyces graminis* on cereals. *Cercospora arachidicola* and *Cercosporidium personata* on peanuts and other Cercospors species on other hosts, for example, sugar beet, bananas, soya beans and rice. *Botrytis cinerea* (grey mould) on tomatoes, strawberries, vegetables, vines and other hosts. Alternaria spp. on vegetables (e.g. cucumber), oil-seed rape, apples, tomatoes and other hosts. *Venturia inaequalis* (scab) on apples. *Plasmopara viticola* on vines. Other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits. *Phytophthora infestans* on potatoes and tomatoes and other Phytophthora spp. on vegetables, strawberries, avocado, pepper, ornamentals, tobacco, cocoa and other hosts. *Thanatephorus cucumeris* on rice and other Rhizoctonia species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against pathogens including Fusarium spp., Septoria spp., Tilletia spp., (bunt, a seed-borne disease of wheat), Ustilage spp. and Helminthosporium spp. on cereals, *Rhizoctonia solani* on cotton and *Pyricularia oryzae* on rice.

The compounds may move acropetally/locally in plant tissue. Moreover, the compunds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposed but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or uniformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide).

The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a slat or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and slats of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Bibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H1,2,4-triazol-1-ylmethyl)butyronitrile, (Z)-N-but-2-enyloxymethyl-2-chloro-2',6'-diethylacetanilide, 1-(2-cyano-2-methoxyiminoacetyl)-3-ethyl urea, 3-(2,4-dichlorophenyl)-2(1H-1,2,4-triazol-1-yl)quinazolin-4(3H)-one, 4-bromo-2-cyano-N,N-dimethyl-6-trifluoromethylbenzimidazole -1-sulphonamide, 5-ethyl-5,8-dihydro-8-oxo(1,3)-dioxol -(4,5-g)quinoline-7-carboxylic acid, α-[N-(3-chloro-2,6-xylyl)-2-methoxyacetamido]-γ-butyrolactone, aldimorph, anilazine, benalaxyl, benomyl, biloxazol, binapacryl, bitertanol, blasticidin S, bromuconazole, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneamino -oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminum, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, empronil metalaxyl, methfuroxam, metsulfovax, myclobutanil, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, SSF-109, streptomycin, sulphur, tebuconazole, techlofthalam, tecnazene, tetraconazole, thiabendazole, thicyofen, thiophanate-methyl, thiram, tolclofos-methyl, triacetate salt of 1,1'-iminodi(octamethylene)diguanidine, triadimefon, triadimenol, triazbutyl, triclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-S-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazine, the auxins (e.g. indoleacetic acid, indolebutyric acid, naphthylacetic acid or naphthoxyacetic acid), the cytokinins (e.g. benzimidazole, benzuladenine, benzylaminopurine, diphenylurea or kinetin), the gibberellins (e.g. $GA_3$, $GA_4$ or $GA_7$) and triapenthenol.

The following Examples illustrate the invention. In the Examples, the term 'ether' refers to diethyl ether, anhydrous magnesium sulphate was used to dry solutions, and solutions were concentrated under reduced pressure. Reactions involving air- or water-sensitive intermediates were performed under an atmosphere of nitrogen and solvents were dried before use, where appropriate. Unless otherwise stated, chromatography was performed on a column of silica gel as the stationary phase. NMR data are selective; no attempt is made to list every absorption in all cases. $^1H$ NMR spectra were recorded using $CDCl_3$-solutions on an instrument operating at 270 MHz, unless otherwise stated. The following abbreviations are used:

DMSO = dimethylsulphoxide
DMF = N,N-dimethylformamide
NMR = nuclear magnetic resonance
IR = infrared
GC = Gas chromatography
TLC = Thin layer chromatography
s = singlet
d = doublet
dd = doublet of doublets
m = multiplet
mp = melting point
ppm = parts per million

EXAMPLE 1

This example illustrates the preparation of (E)- and (Z)-methyl O-methyl-2-[2-(6-(2-cyanophenoxy)pyrimidin-4-yloxy)phenyl]oximinoacetate (compounds Nos. 9B and 9A, respectively, of Table I).

To a solution of 4,6-dichloropyrimidine (0.76 g, 5.10 mmol) in dry DMF (4 ml) at 0° C. was added anhydrous potassium carbonate (0.70 g, 5.10 mmol). A solution of (E)-methyl 2-(2-hydroxypenyl)-3-methoxypropenoate (0.53 g, 2.55 mmol, prepared as described in Example 3 of EP-A-0242081) in dry DMF (2 ml) was then added dropwise with stirring. After the addition was complete, the reaction mixture was allowed to warm to room temperature and stirring was continued over the weekend. The reaction mixture was then diluted with water (15 ml) and extracted with ether (3×20 ml). The combined ether extracts were washed with brine and dried. Evaporation afforded a brown liquid (1.10 g) which was chromatographed (eluent etherin-hexane, 3:2) to give (E)-methyl 2-[2-(6-chloropyrimidin-4-yloxy)phenyl]-3-methoxypropenoate as a thick, pale yellow oil (0.58 g, 71% yield) which crystallised on standing. Recrystallisation from ether/dichloromethane (trace)/n-hexane at −78 C. gave the product as a white powder (0.25 g), mp 94°-5° C. In a separate preparation, 15 g of product was obtained from 4,6-dichloropyrimidine (15.90 g), (E)-methyl 2-(2-hydroxyphenyl)-3-methoxypropeoate (14.80 g) and anhydrous potassium carbonate (19.64 g).

(E)-Methyl 2-[2-(6-chloropyrimidin-4-yloxy)phenyl]-3-methoxypropenoate (1.50 g, 4.68 mmol) was heated overnight at 95°-100° C. with 2-cyanophenol (0.61 g, 5.15 mmol) and potassium carbonate (0.71 g, 5.15 mmol) in DMF (35 ml) in the presence of a catalytic amount of copper (I) chloride. The reaction mixture was cooled, diluted with water and then extracted with ether. The combined ether layers were washed with 2M aqueous sodium hydroxide solution and brine and then dried. Evaporation of the solvent gave a pale yellow oil (1.52 g). Recrystallisation from ether/dichloromethane/n-hexane gave (E)-methyl 2-[2-(6-(2-cyanophenoxy)-pyrimidin-4-yloxy)phenyl]-3-methoxypropenoate as a pale yellow powder (1.20 g, 64% yield), mp 110°-111° C.; $^1H$ NMR δ 3.63(3H,s), 3.74(3H,s), 6.42(1H,s), 7.19-7.47(6H,m), 7.50(1H,s), 7.62-7.75(2H,m), 8.40(1H,s) ppm. In a subsequent preparation of this intermediate, recrystallisation gave a white crystalline solid, mp 118°-119° C.

To a vigorously stirred mixture of water (20 ml) and a solution of (E)-methyl 2-[2-(6-(2-cyanophenoxy)-pyrimidin-4-yloxy)phenyl]-3-methoxypropenoate (3.2 g, 7.94 mmol) in dichloromethane (20 ml) was added potassium permanganate (2.5 g, 15.9 mmol) in one portion and tetra-n-hexylammonium hydrogen sulphate (200 mg). The reaction mixture was stirred overnight (16 hours) and then filtered. The filter was washed through with ether and water and then the combined filtrates were extracted with ether (×3). The ether extracts were washed with water (×3) and brine (×1), dried, filtered and evaporated. The residue was chromatographed (eluent dichloromethaneacetone, 98:2). Recrystallisation (ether-pentane) of the major component afforded methyl 2-[2-(6-(2-cyanophenoxy)pyrimidin-4-yloxy)phenyl]-ketoacetate (2.105 g, 71%) as a white crystalline solid; mp 96°-97° C.; $^1H$ NMR ($CDCl_3$) δ 3.83(3H,s), 6.61(1H,s), 7.27-7.47(4H,m), 7.67-7.76(3H,m), 8.02(1H,dd), 8.39(1H,s) ppm; IR maxima 2234(CN), 1743(CO, ester); 1688(CO, ketone)cm$^{-1}$.

To a solution of the ketoester (500 mg, 1.33 mmol) in dry methanol (10 ml) was added methoxylamine hydrochloride (112 mg, 1.33 mmol). After stirring at room temperature for 4 hours, more methoxylamine hydrochloride (66 mg) was added and stirring was continued overnight. The complete disappearance of the starting ketoester was demonstrated by loss of the peak at 1688 cm$^{-1}$ in the IR spectrum. The reaction mixture was worked up and then repeatedly chromatographed (eluent dichloromethane-acetone mixtures) to afford, in order of increasing polarity, (Z)-methyl 0-methyl-2-]2-(6-(2-cyanophenoxy)pyrimidin-4-yloxy)phenyl]oximinoacetate ("Isomer A", Compound No. 9A of Table I) as a white foam (75 mg, 14%); $^1$H NMR (CDCl$_3$) δ3.78(3H,s), 3.98(3H,s), 6.50(1H,s), 7.18(1H,d), 7.31–7.41(3H,m), 7.48–7.54(1H,m), 7.66–7.81(3H,m), 8.38(1H,s) ppm; IR maxima 2242 (CN), 1741(CO) cm$^{-1}$; mass spectrum (EI) 404 (M+); (CI) 422 (M+NH$_4$+), 405 (MH+); and (E)-methyl O-methyl-2-]2-(6-(2-cyanophenoxy)pyrimidin-4-yloxy)phenyl]-oximinoacetate ("Isomer B", Compound No. 9B of Table I) as an off-white solid (403 mg, 75%); mp 125°–127° C.; $^1$H NMR (CDCl$_3$) δ 3.81(3H,s), 3.94(3H,s), 6.51(1H,s), 7.27–7.43(4H,m), 7.49–7.55(1H,m), 7.65–7.73(3H,m), 8.39(1H,s) ppm; IR maxima 2234 (CN), 1728 (CO) cm$^{-1}$; mass spectrum (EI) 404 (M$^{30}$ ); (CI) 422 (M+NH$_4$+), 405 (MH+).

The following are examples of compositions suitable for agricultural and horticultural purposes which can be formulated from the compounds of the invention. Such compositions form another aspect of the invention. Percentages are by weight.

EXAMPLE 2

An emulsifiable concentrate is made up by mixing and stirring the ingredients until all are dissolved.

| | |
|---|---|
| Compound No. 9B of Table I | 10% |
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 3

The active ingredient is dissolved in methylene dichloride and the resultant liquid sprayed on to the granules of attapulgite clay. The solvent is then allowed to evaporate to produce a granular composition.

| | |
|---|---|
| Compound No. 9B of Table I | 5% |
| Attapulgite granules | 95% |

EXAMPLE 4

A composition suitable for use as a seed dressing is prepared by grinding and mixing the three ingredients.

| | |
|---|---|
| Compound No. 9B of Table I | 50% |
| Mineral oil | 2% |
| China clay | 48% |

EXAMPLE 5

A dustable powder is prepared by grinding and mixing the active ingredient with talc.

| | |
|---|---|
| Compound No. 9B of Table I | 5% |
| Talc | 95% |

EXAMPLE 6

A suspension concentrate is prepared by ball milling the ingredients to form an aqueous suspension of the ground mixture with water.

| | |
|---|---|
| Compound No. 9B of Table I | 40% |
| Sodium lignosulphonate | 10% |
| Bentonite clay | 1% |
| Water | 49% |

This formulation can be used as a spray by diluting into water or applied directly to seed.

EXAMPLE 7

A wettable powder formulation is made by mixing together and grinding the ingredients until all are thoroughly mixed.

| | |
|---|---|
| Compound No. 9B of Table I | 25% |
| Sodium lauryl sulphate | 2% |
| Sodium lignosulphonate | 5% |
| Silica | 25% |
| China clay | 43% |

EXAMPLE 8

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on Erysiphe graminis in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace -5% of disease on untreated plants
2 = 6-25% of disease on untreated plants
1 = 26-59% of disease on untreated plants
0 = 60-100% of disease on untreated plants
The results are shown in Table IV.

TABLE IV

| Compound No. | Table No | Puccinia Recondita (Wheat) | Erysiphe Graminis Tritici (Wheat) | Septoria Nodorum (Wheat) | Venturia Inaequalis (Apples) | Pyricularia Oryzae (Rice) | Plasmopara Viticola (Vines) | Phytophthora Infestans (Tomatoes) |
|---|---|---|---|---|---|---|---|---|
| 9A | I | 4a | 0a | 0a | 4a | 0a | 4a | 4a |
| 9B | I | 4 | 3 | 4 | 4 | 4 | 4 | 3 | a 10 ppm foliar spray only

CHEMICAL FORMULAE
(in description)

(I) — structure with substituents A, G, U, X, Q, K, L, D, M, Y, V, C, CH$_3$O$_2$C, N.OCH$_3$ (E) and (Z) isomers referred to on page 1

TABLE I — (I.1) structure

TABLE II — (I.2) structure (I.3) structure with Ar (I.4) structure with Z

-continued
CHEMICAL FORMULAE
(in description)

TABLE III — (I.5) structure with Z

*X of Compound No 146 is 2-(isoxazolinone)

*X of Compound No 147 is 2-(thiazolidinedione)

*X of Compound No 148 is 2-(thiazine)

*X of Compound No 149 is 2-(oxazinedione)

*Ar of Compound No 161 is quinoline

*Ar of Compound No 162 is naphthyl

*Ar of Compound No 163 is naphthyl

*Ar of Compound No 164 is benzodioxole

*Ar of Compound No 165 is benzothiophene

*Ar of Compound No 166 is benzimidazole

*Ar of Compound No 198 is cyanonaphthyl (CN)

*Ar of Compound No 199 is cyanoquinoline (CN)

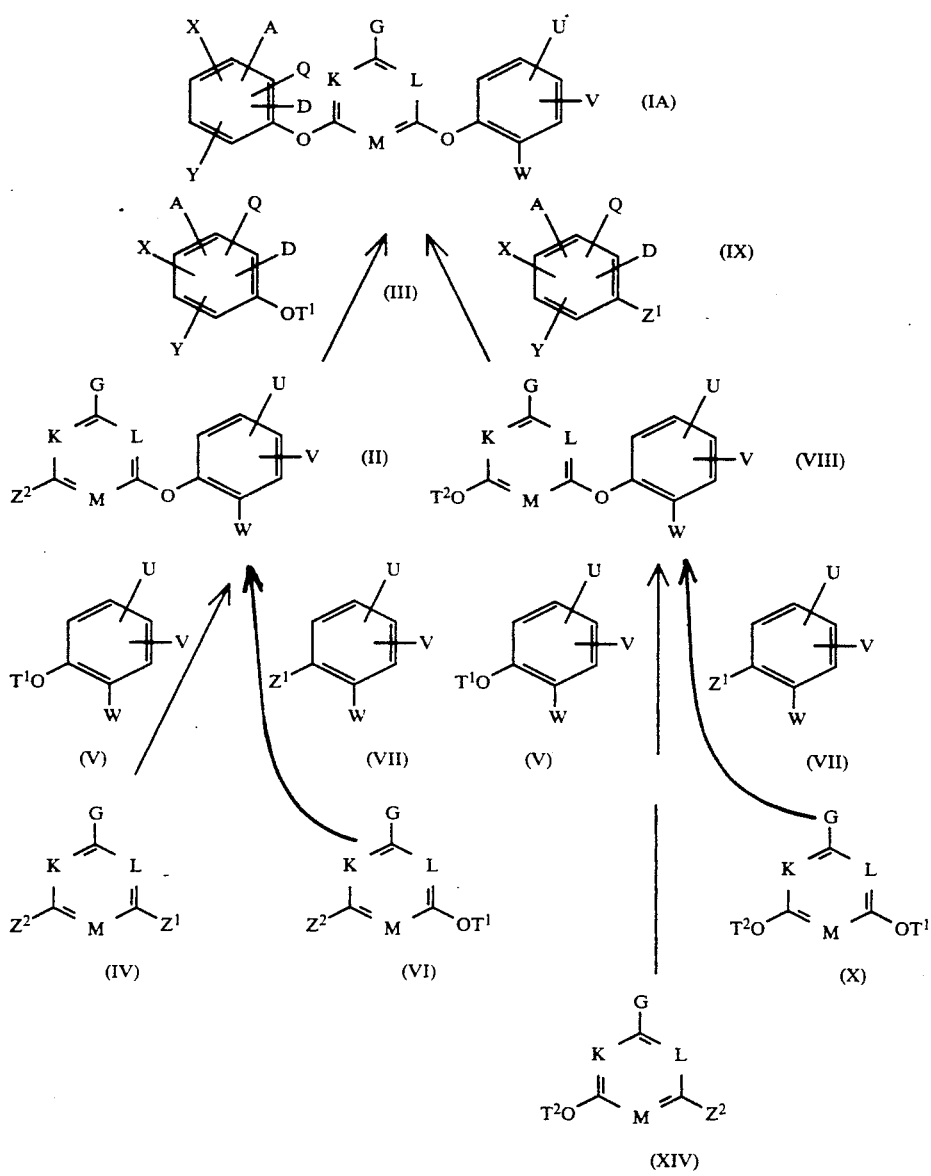
Scheme I
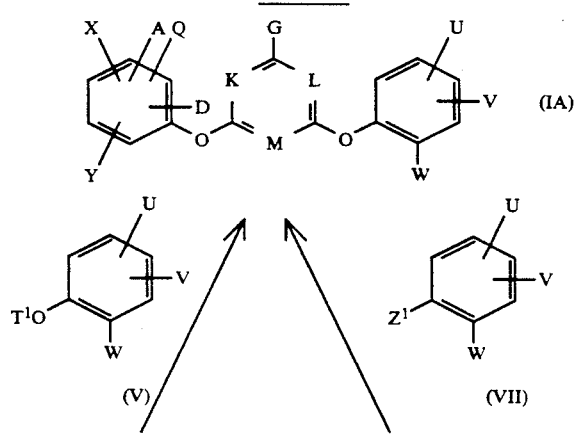
Scheme II

Scheme II

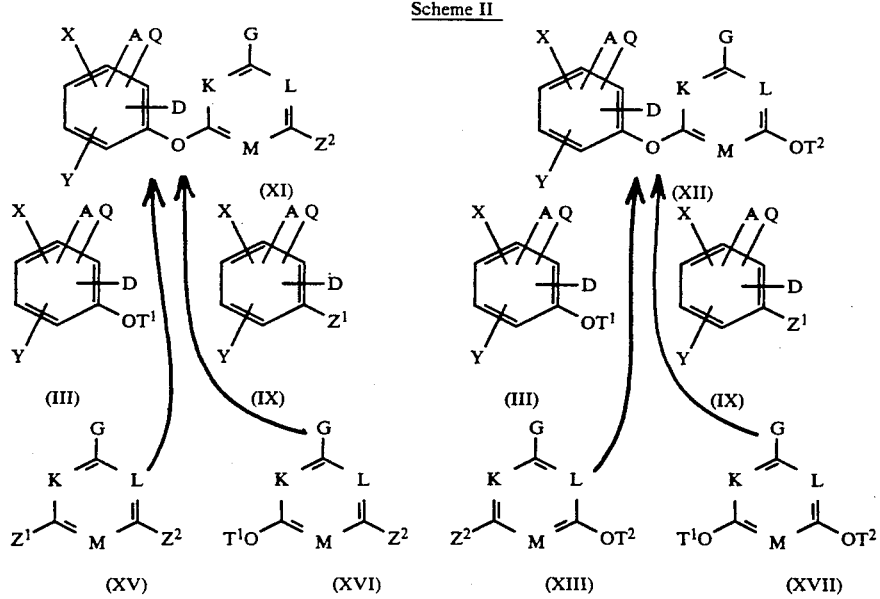

We claim:

1. A compound having the formula (I):

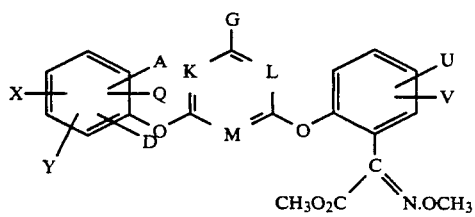

in which any two of K, L and M are nitrogen and the other is CE; X and Y are independently hydrogen, halogen, $C_{1-4}$ alkyl, $C_{3-6}$ cycloalkyl, $C_{2-4}$ alkenyl, $C_{2-4}$ alkynyl, $C_{2-4}$ alkynyloxy, phenyl, benzyloxy, cyano, isocyano, thiocyanato, isothiocyanato, nitro, $NR^1R^2$, $NR^1OR^2$, $N_3$, $NHCOR^1$, $NR^1CO_2R^2$, $NHCONR^1R^2$, $N=CHNR^1R^2$, $NHSO_2R^1$, $OR^1$, $OCOR^1$, $OSO_2R^1$, $SR^1$, $SOR^1$, $SO_2R^1$, $SO_2OR^1$, $SO_2NR^1R^2$, $COR^1$, $CR^1=NOR^2$, $CHR^1CO_2R^2$, $CO_2R^1$, $CONR^1R^2$, $CSNR^1R^2$ $CH_3O_2C.C=CH.OCH_3$, $CH_3O_2C.C=N.OCH_3$, or 1-(imidazol-1-yl); or X and Y, when ortho to one another, together form methylenedioxy, or together with the phenyl ring to which they are attached form a naphthalene, quinoline, benzimidazole or benzothienyl ring; A, Q, D, E, G, U and V are independently hydrogen, halogen, $C_{1-4}$ alkyl, $C_{1-4}$ alkoxy, cyano, nitro or trifluoromethyl; and $R^1$ and $R^2$ are independently hydrogen, $C_{1-4}$ alkyl or phenyl; the aliphatic moieties of any of the foregoing being optionally substituted with one or more halogen, cyano, $OR^1$, $SR^1$, $NR^1R^2$, $Sir^1_3$, or $OCOR^1$ and the phenyl moieties of any of the foregoing being optionally substituted with one or more of halogen, $C_{1-4}$ alkyl, $C_{1-4}$ alkoxy, nitro or cyano.

2. Compounds according to claim 1 in which any two of K, L and M are nitrogen and the other is CH; A, Q, D, G, U and V are all hydrogen; X is hydrogen, halogen, $C_{1-4}$ alkyl, $C_{1-4}$ alkyl substituted with halogen, hydroxy, cyano, $C_{1-4}$ alkoxy or $C_{1-4}$ alkanoyloxy, $C_{2-4}$ alkenyl, alkenyl, $C_{2-4}$ alkynyl, $C_{2-4}$ alkenyloxy, thiocyanato, $C_{2-4}$ alkynyloxy, phenyl, benzyl, cyano, isocyano, isothiocyanato, nitro, amino, mono- or di($C_{1-4}$)alkylamino, formylamino, $C_{1-4}$ alkanoylamino, benzoylamino, ureido, phenylureido, $C_{1-4}$ alkylsulphonylamino, phenylsulphonylamino, hydroxy, $C_{1-4}$ alkoxy, phenoxy, $C_{1-4}$ alkanoyloxy, $C_{1-4}$ alkylsulphonyloxy, phenylsulphonyloxy, $C_{1-4}$ alkylthio, $C_{1-4}$ alkylsulphinyl, $C_{1-4}$ alkylsulphonyl, formyl, $C_{1-4}$ alkanoyl, benzoyl, hydroxyimino-($C_{1-4}$)alkyl, $C_{1-4}$ alkoxyimino($C_{1-4}$)alkyl, carbamoyl, $C_{1-4}$ alkylcarbamoyl, thiocarbamoyl or $C_{1-4}$ alkylthiocarbamoyl, the phenyl ring of any of the foregoing being optionally substituted with halogen, $C_{1-4}$ alkyl, $C_{1-4}$ alkoxy, nitro or cyano; and Y is halogen, $C_{1-4}$ alkyl, $C_{1-4}$ alkoxy, nitro, cyano or hydrogen; or X and Y, when ortho to one another, together form methylenedioxy, or together with the phenyl ring to which they are attached form a naphthalene, quinoline, benzimidazole or benzothienyl ring.

3. Compounds according to claim 2 in which X is attached to the 2-position of the phenyl ring.

4. Compounds having the formula (I.1):

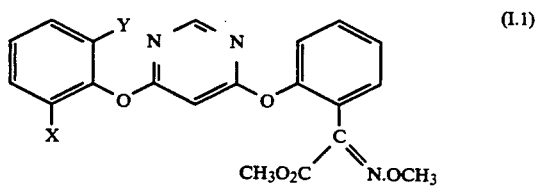

in which X is hydrogen, halogen, $C_{1-4}$ alkyl, $C_{1-4}$ alkoxy, trifluoromethyl, cyano, thiocarbamoyl or nitro, and Y is hydrogen or fluoro.

5. A fungicidal composition comprising a fungicidally effective amount of a compound according to claim 1 and a fungicidally acceptable carrier or diluent therefor.

6. A method of combating fungi which comprises applying to plants, to the seeds of plants or to the locus of the plant or seeds, a compound according to claim 1 or a composition according to claim 5.

* * * * *